United States Patent [19]

Vince

[11] Patent Number: 5,348,528
[45] Date of Patent: Sep. 20, 1994

[54] CARDIAC ASSIST DEVICE

[75] Inventor: Dennis J. Vince, Vancouver, Canada

[73] Assignee: Vince Medical Company Limited, Vancouver, Canada

[21] Appl. No.: 53,059

[22] Filed: Apr. 26, 1993

[51] Int. Cl.⁵ .................. A61N 1/362; A61M 1/12
[52] U.S. Cl. ........................................................ 600/16
[58] Field of Search ............... 600/16, 17, 18; 623/3

[56] References Cited

U.S. PATENT DOCUMENTS

| | | | |
|---|---|---|---|
| 4,185,617 | 1/1980 | Hutchins | 623/3 |
| 5,098,370 | 3/1992 | Rahat et al. | 600/16 |

*Primary Examiner*—George Manuel
*Attorney, Agent, or Firm*—Townsend and Townsend Khourie and Crew

[57] ABSTRACT

Apparatus to assist a patient's heart. The apparatus includes a main pump to be mounted on the patient's chest wall. The pump is able to reciprocate to generate a compression stroke and an expansion stroke. The pump includes a pump chamber to contain a fluid. An atrial pump is attached to the atrium of the patient's heart. The atrium receives blood through the patient's inferior vena cava. A conduit communicates the pump chamber and the atrial pump. There is a by-pass in the conduit to surround the inferior vena cava. The arrangement is such that the compression stroke of the pump forces fluid in the by-pass to restrict the inferior vena cava and compress the atrium to pump blood towards the patient's pulmonary artery.

14 Claims, 5 Drawing Sheets

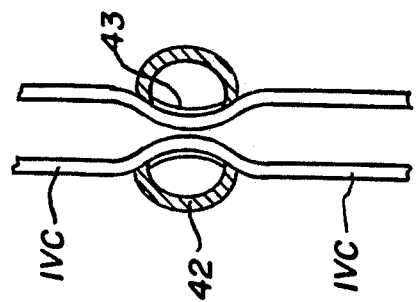
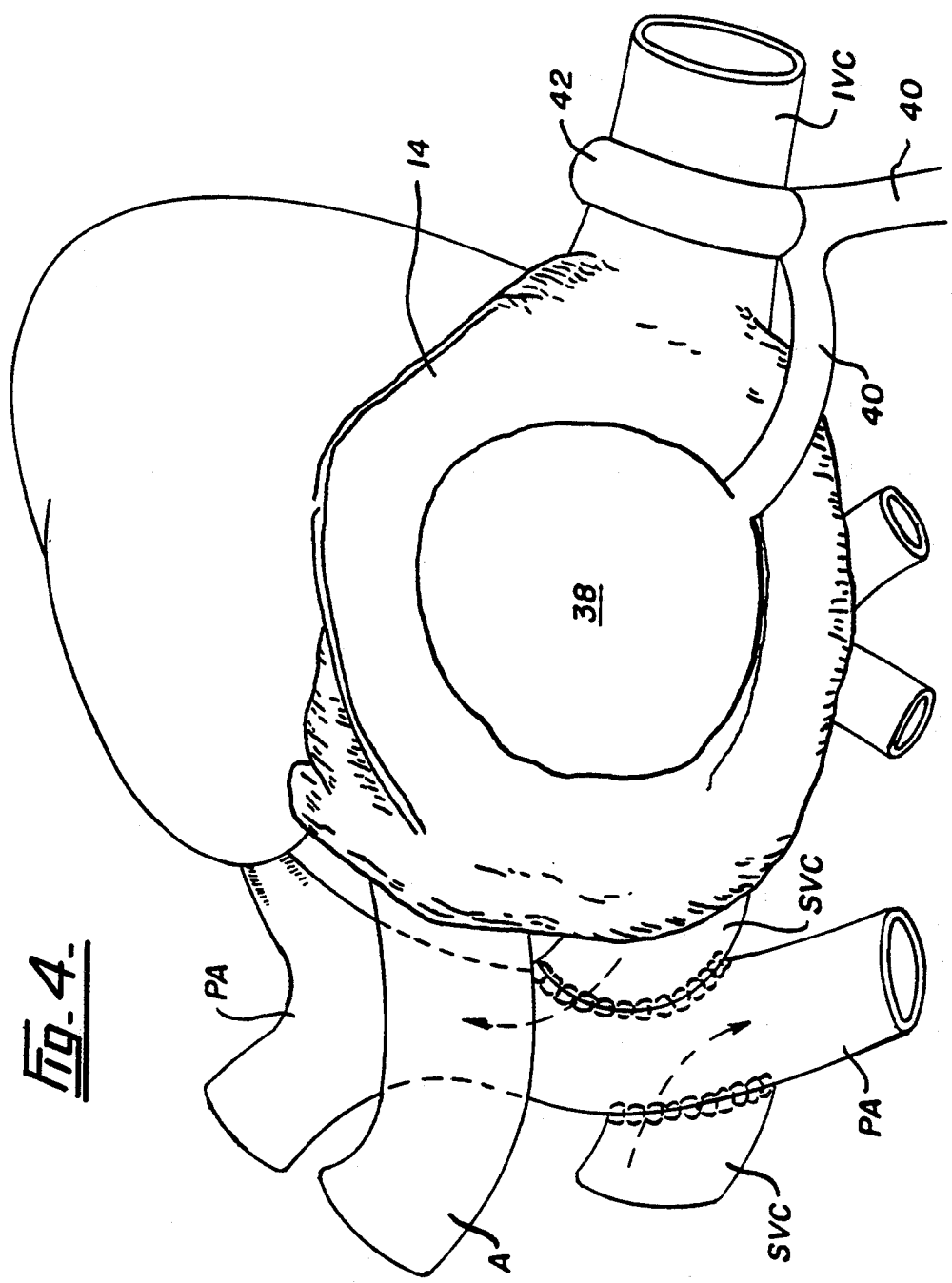

5,348,528

CARDIAC ASSIST DEVICE

FIELD OF THE INVENTION

This invention relates to an apparatus to assist a patient's heart. More particularly the apparatus is a cardiac assist device capable of being adapted for use as a left or right ventricle assist device and, in a preferred embodiment, as an assist for the right ventricle substitute, that is a modified right atrium, subsequent to the Fontan operation.

DESCRIPTION OF THE PRIOR ART

The Fontan operation has become of increasing importance over the past two decades for younger patients with complex univentricular hearts. Prior to the Fontan procedure such a condition was considered inoperable and untreatable.

The main risk factors for the Fontan operation include decreased systolic function of the ventricle, increased pulmonary vascular resistance and valve regurgitation.

Long term difficulties are now more frequently observed. Surviving patients experience reduced systolic function and increased pulmonary vascular resistance.

There have been modifications of the operation. For example the fenestrated Fontan procedure reduces the initial mortality of high risk patients but may not reduce the long term complications. As a result there is a belief that the Fontan operation should be considered a temporary procedure, and patients will require a heart-lung transplantation at a later age.

In the Fontan operation the systemic venous return is connected to the pulmonary artery by by-passing an absent or defective ventricle. The operation takes two forms. First closure of the atrial septal defect and anastomosis of the right atrium to the pulmonary artery and, secondly, construction of a tunnel within the right atrium, connecting the inferior vena cava to the superior vena cava and then connecting the superior vena cava to the pulmonary artery.

SUMMARY OF THE INVENTION

The present invention seeks to further improve the art and provides an alternative to transplantation. The present invention provides a right atrial assist that has the capability of prolonging the duration and improving the quality of the life of many patients who otherwise would have a heart/lung transplantation as their only opportunity for survival.

Accordingly, the present invention provides an apparatus to assist a patient's heart comprising a main pump to be mounted on the patient's chest wall and able to reciprocate to generate a compression stroke and an expansion stroke, said pump including a pump chamber to contain a fluid; an atrial pump attached to the atrium of the patient's heart, said atrium receiving blood through the patient's inferior vena cava (IVC); a conduit communicating the pump chamber and the atrial pump; a bypass in the conduit to surround the IVC; whereby the compression stoke of the pump forces fluid in the bypass to restrict the IVC and compresses the atrium to pump blood towards the patient's pulmonary artery.

DESCRIPTION OF THE DRAWINGS

The invention is illustrated, by way of example, in the drawing in which:

FIG. 4 is an external view of a heart fitted part of the apparatus of the present invention;

FIG. 4a is a detail of FIG. 4;

DESCRIPTION OF THE PREFERRED EMBODIMENTS

Figure 1:
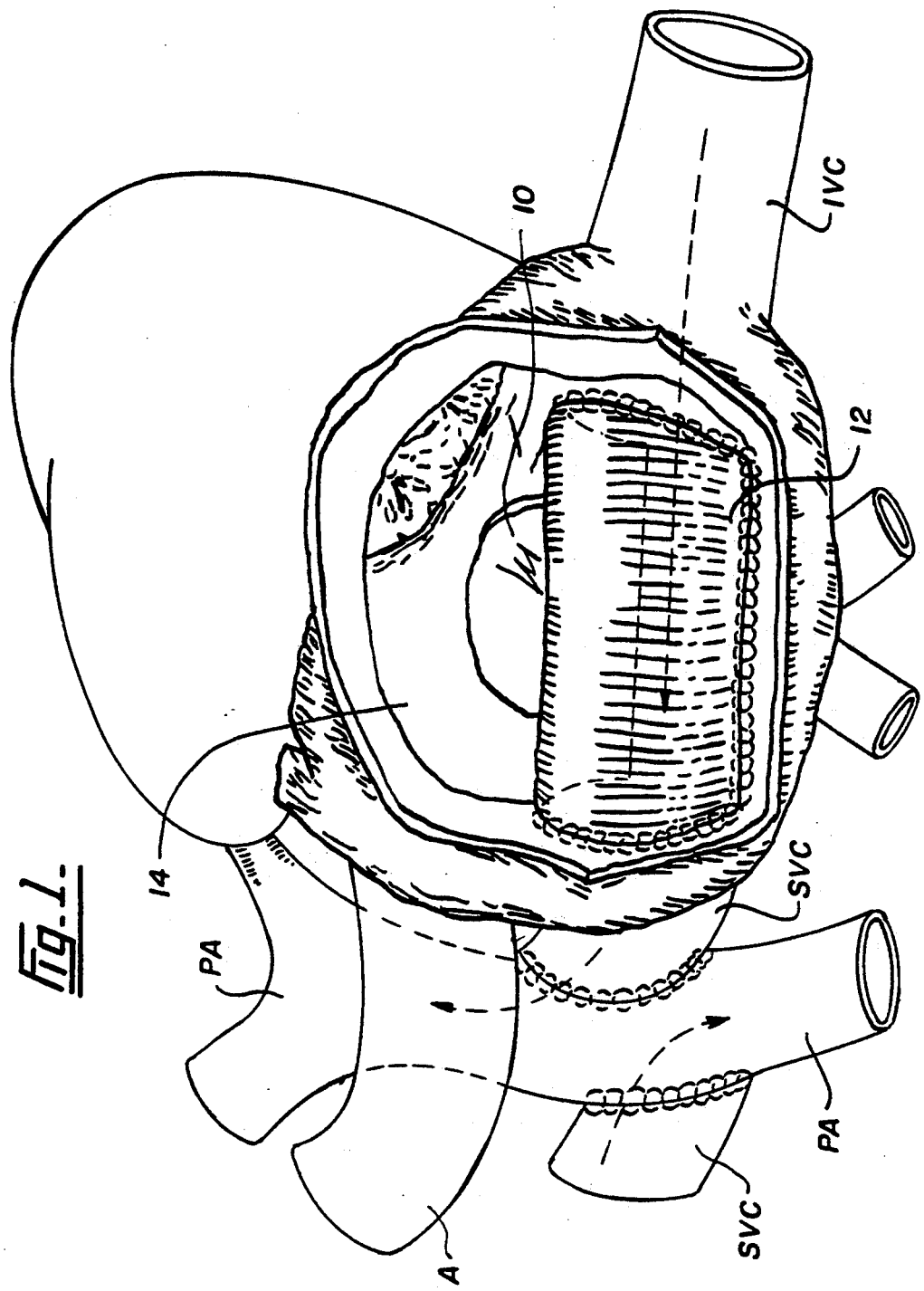
FIG. 1 illustrates a heart with a right atrial tunnel type of the Fontan procedure.
Figure 2:
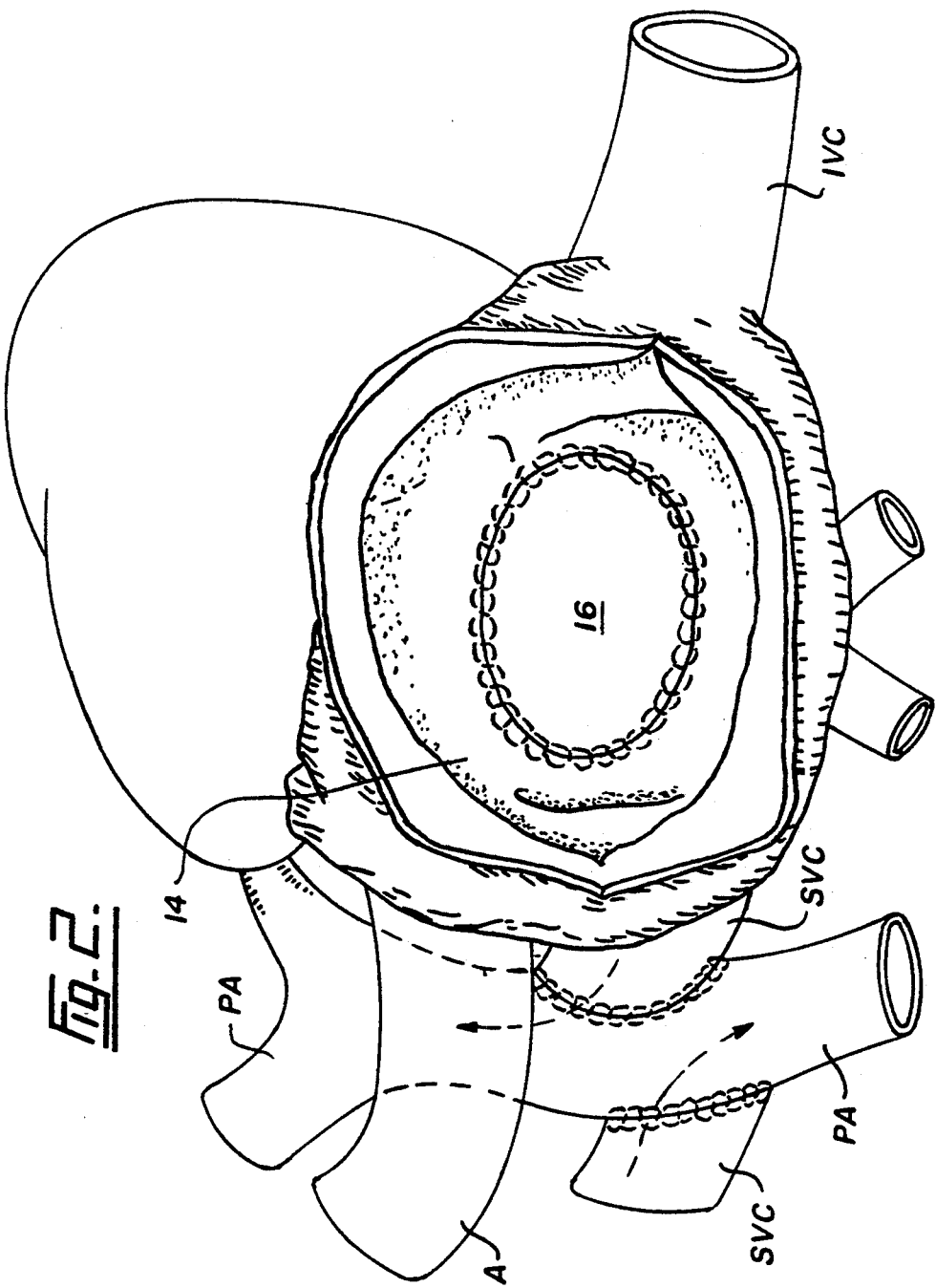
FIG. 2 illustrates a heart with an atrial septal defect type of Fontan procedure.

FIGS. 1 and 2 show a heart modified according to the Fontan operation. FIG. 1 shows an atrial septal defect 10 and a lateral tunnel 12 connecting the inferior vena cava IVC to the superior vena cava SVC. The superior vena cava SVC is connected to the pulmonary artery PA and the blood flow in the superior vena cava SVC thus re-directed. The aorta A is also shown. Thus FIG. 1 shows construction of a tunnel 12 inside an atrium 14 and connecting the inferior vena cava IVC to the superior vena cava SVC. The superior vena cava SVC is connected to the pulmonary artery PA.

In FIG. 2 the second Fontan technique is illustrated. The atrial septal defect 10 is repaired by a patch 16. Again the superior vena cava SVC is connected to the pulmonary artery PA. The right atrium 14 is connected to the pulmonary artery PA via the superior vena cava SVC.

FIGS. 3 to 6 illustrate the present invention.

Figure 3:
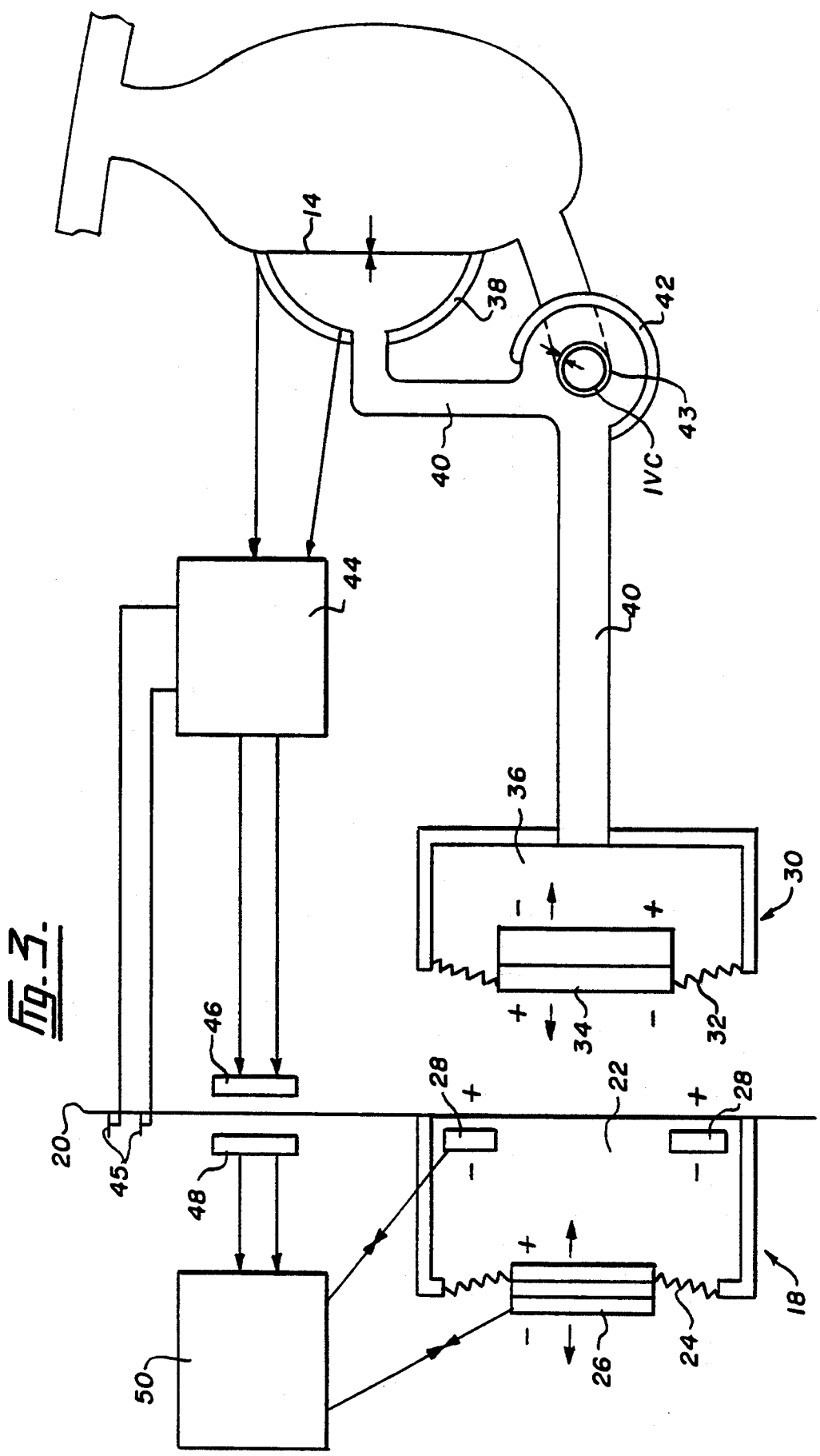
FIG. 3 is a schematic view of the apparatus according to the present invention.

FIG. 3 shows the apparatus schematically. There is a main pump 18 to be mounted on the exterior of the patient's chest wall 20. The main pump has a chamber 22 defined between a pump diaphragm 24 and the skin on the chest wall 20 of the patient. There is a magnet 26 attached to the diaphragm 24 and an electromagnet 28 attached to the skin of the patient.

On the interior of the patient's chest, immediately adjacent the main pump 18, there is a hydraulic pressure receiver 30 formed with a diaphragm 32 mounting a magnet 34 and having a chamber 36. There is an atrial pump 38 attached to an atrium 14 of the patient's heart. The atrium 14 receives blood from the patient's inferior vena cava IVC. A conduit 40 having rigid walls communicates the chamber 36 and the atrial pump 38. There is a by-pass 42 in the conduit 40 that surrounds the inferior vena cava IVC.

By-pass 42 includes a flexible inner wall or sleeve 43 that surrounds the inferior vena cava IVC. Electrodes 45 assesses heart activity. The electrodes 45 generates a signal which is transmitted to an internal sensor transmitter 44. The internal sensor transmitter 44 communicates with an internal transcutaneous signal transmitter 46 which, in turn, communicates with an external transcutaneous signal transmitter 48. A signal from the external transcutaneous signal transmitter 48 is sent to an electrical pulse generator 50 that includes a commutator, a timer and a power source. The electrical pulse generator is, in turn, in communication with the magnets 26 and 28 of the main pump 18.

Although not shown in the drawings, main pump 18 has a diaphragm that seals the chamber 22 and contacts the skin of the chest wall 20. Diaphragm 32 seals chamber 36 of the hydraulic pressure receiver 30. Similarly atrial pump 38 is closed with a diaphragm that contacts the atrium wall. Thus the system of hydraulic pressure receiver 30, conduit 40, atrial pump 38 and by-pass 42 with sleeve 43 forms a closed circuit. This arrangement is necessary to avoid leakage of the fluid contained within the system by which pressure is transmitted.

Figure 5:
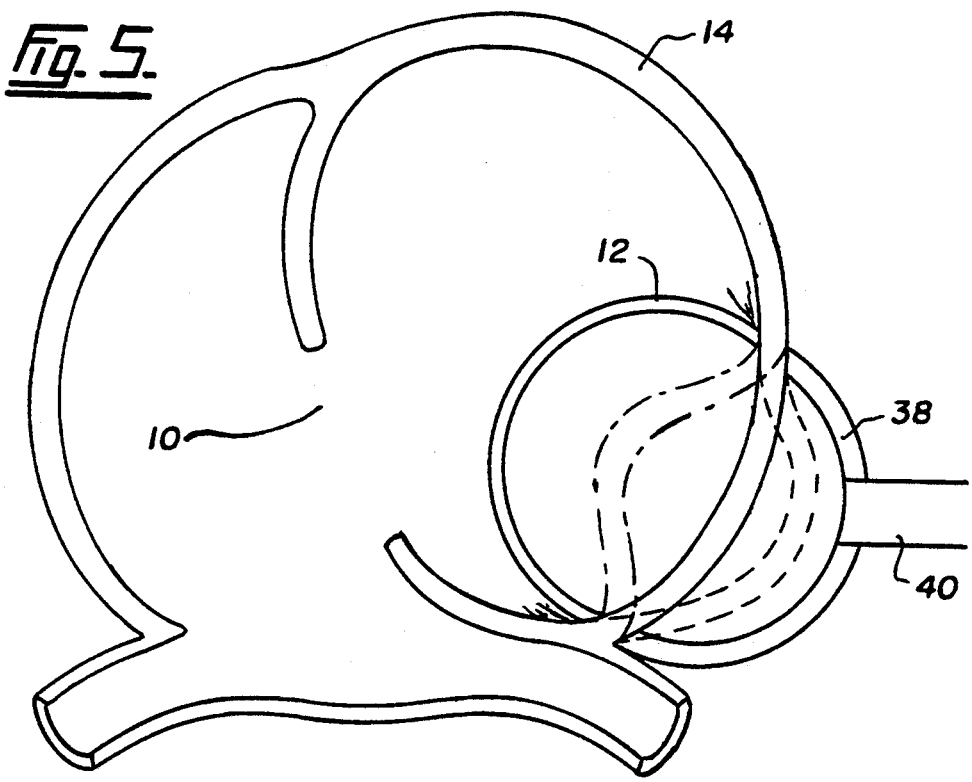
FIG. 5 illustrates operation of the device according to the present invention in the heart of FIG. 1.
Figure 6:
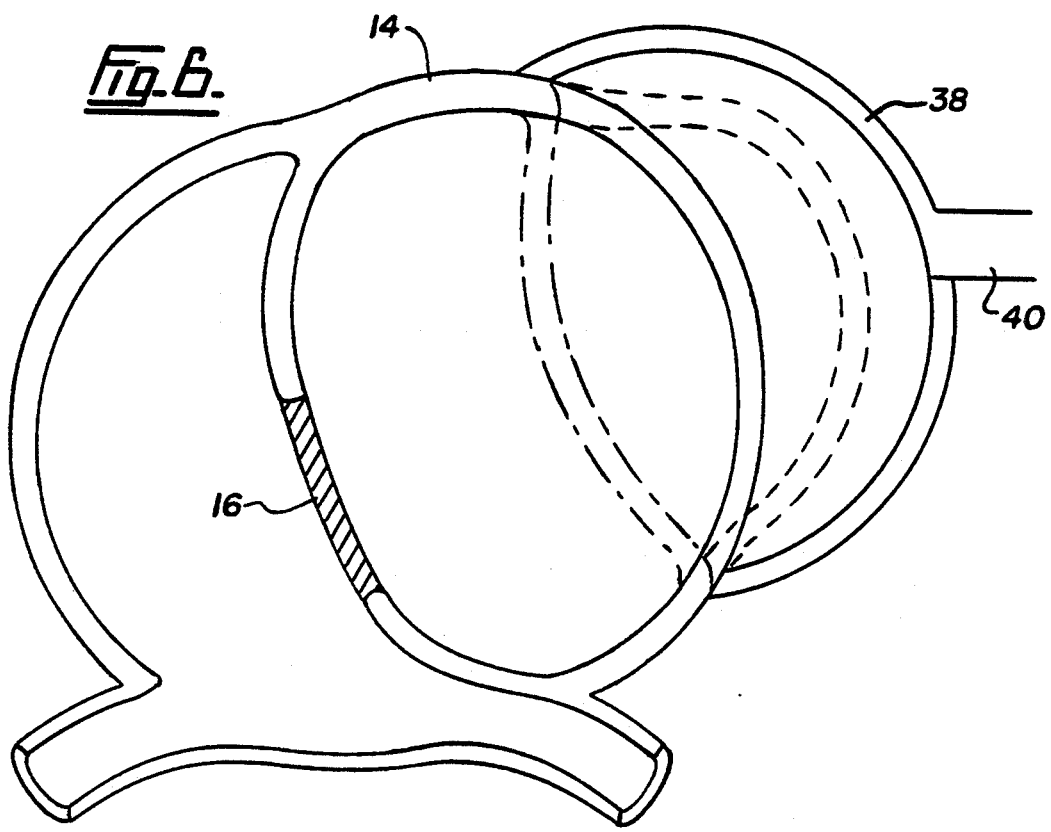
FIG. 6 illustrates operation of the apparatus the present invention in the heart of FIG. 2.

An external view of the by-pass 42 is shown in FIG. 4 and operation of the device is shown in FIGS. 4a, 5 and 6.

FIG. 4 illustrates the atrial pump 38 located on the right atrium 14 of the patient and the rigid conduit 40 that extends from the hydraulic pressure receiver 30 to the atrial pump 38 with the by-pass 42 extending around the inferior vena cava IVC.

The apparatus of FIG. 4 functions as follows: The main pump 18 receives an electrical pulse from the electrical pulse generator 50 which activates the magnets 26 and 28. The diaphragm 24 moves in a manner controlled by the direction of the current from the electrical pulse generator 50 by attraction and repulsion of magnets 26 and 28. Movement of the diaphragm 24 generates positive and negative hydraulic pressure in the chamber 22 of the main pump 18. The chamber 28 is in contact with the skin surface which reacts to those internal pressure changes by moving inwards and outwards. This movement is transmitted to the diaphragm 32 of hydraulic pressure receiver 30. The movement is accentuated by the presence of magnet 34 in the hydraulic pressure receiver 30. That is the magnet 34 is repulsed or attracted, depending on the variation of the polarity of the magnets 28. Thus diaphragm movement by hydraulic pressure is assisted by magnetic force. Movement of the diaphragm 32 creates alternatively positive and negative pressure within the hydraulic pressure receiver 30 as a result of movements in the main pump 18. Hydraulic pressure in the hydraulic pressure receiver 30 is transmitted through the conduit 40, through the by-pass 42 that surrounds the inferior vena cava IVC and to the atrial pump 38.

When pressure is applied to the conduit 40 the inferior vena cava IVC is restricted by that pressure (as shown in FIG. 4a). Similarly, of course, when there is reduced pressure in the hydraulic pressure receiver 30 then the inferior vena cava is opened as pressure within the inferior vena cava exceeds the pressure within the by-pass 42. The rigidity of conduit 40 means that it does not change volume with pressure changes in receiver 30. Similarly atrial pump 38 and by-pass 42 have rigid walls (as emphasized by the use of double lines in FIG. 3).

The increased hydraulic pressure in receiver 30 is transmitted to the atrial pump 38 and to the atrial chamber. The motion of the atrial pump 38 will increase the pressure in the right atrium and, because of the closure of the inferior vena cava, forward flow from the right atrium toward the pulmonary artery will occur.

When the pressure is reduced and the inferior vena cava opened by the reduced pressure, the atrial pump 38 will move the atrium wall outwardly, reducing pressure within the atrium 14. Blood flow from the inferior vena cava to the right atrium 14 will then fill the atrium. The cycle can then be repeated.

The electrodes 45 and the hydraulic pressure sensors sense the electrophysiology of the heart and the function of the hydraulic pressure received, the atrial pump 38 and the by-pass 42. This information is amplified and transmitted by the internal sensor transmitter 44, which is powered by an internal battery. The signal generated is transmitted through the skin using transcutaneous induction coils as known in the art. The external sensor 48 transmits a signal to the electrical pulse generator 50. The electrical pulse generator 50 contains a timer which coordinates the function of the atrial pump 38 and the by-pass 42 to the patient's heart function, thus maximizing the forward flow from the inferior vena cava to the right atrium and from the right atrium toward the pulmonary artery. The information received from the pressure sensors assists this function. The electrical pulse generator 50 contains a commutator (not shown) which, by reversing direction of electrical current to the magnets 26 and 28 in the main pump 18, changes the hydraulic pressure in the pump 18. This variation results in a similar change throughout the hydraulic system. Repetitive cycles of the change create the pumping action of the device. The electrical pulse generator 50 has a power source which is, of course, easily renewable.

Thus the apparatus of the present invention enhances the forward flow of blood from the IVC to the left atrium via pulmonary artery circulation. It does this by pumping blood forward from the right atrium, or right atrium lateral tunnel, to the pulmonary artery. Power generated outside the body is transmitted by hydraulic force. The alternating pressure in the conduit 42 is generated by electromagnetic energy and mechanical energy transmitted through the skin surface.

The invention has been described with reference to assisting a heart that has undergone the Fontan procedure. The invention is also related to extraluminal hydraulic valve and implanted systolic and diastolic assist devices.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

I claim:

1. Apparatus to assist a patient's heart comprising:
    a main pump adapted to be mounted to a patient's chest wall and including a pump chamber containing a fluid, the main pump having means for generating a compression stroke and an expansion stroke;
    an atrial pump adapted to be attached to an atrium of the patient's heart, said atrial pump having means for compressing the atrium;
    means for coupling the atrial pump to the main pump so that the compressing means compresses the atrium when the generating means generates the compression stroke thereby pumping blood towards the patient's pulmonary artery; and
    a bypass adapted to surround the patient's inferior vena cava, said bypass having means for restricting the inferior vena cava when the generating means generates the compression stroke thereby pumping blood towards the patient's pulmonary artery.

2. Apparatus as claimed in claim 1 wherein:
    said coupling means comprises a conduit fluidly coupled to said atrial said bypass.

3. Apparatus as claimed in claim 1 wherein:

the coupling means comprises a pressure receiver adapted to be mounted on the chest wall and beneath the skin, and being fluidly coupled to said pressure receiver.

4. Apparatus as claimed in claim 3 wherein:

said main pump includes a chamber and a pump diaphragm, the pump diaphragm being adapted to be positioned adjacent the patient's skin;

a magnet attached to the diaphragm;

at least one electro magnet spaced apart from said magnet and adapted to be mounted adjacent the skin of the patient; and means for supplying a current to the at least one electromagnet, the supplying means having means for varying the polarity of the current;

whereby the diaphragm reciprocates upon varying the polarity of the current applied to the at least one electro magnet.

5. Apparatus as claimed in claim 4 wherein the pressure receiver comprises:

a receiver diaphragm adapted to be mounted adjacent the patient's skin, the receiver diaphragm being reciprocally movable; and a magnet attached to the receiver diaphragm, said magnet being attracted to, and repelled by, said at least one electro magnet of the main pump to reciprocate the receiver diaphragm thereby providing a pumping action.

6. Apparatus as claimed in claim 4 further comprising:

at least one electrode, said electrode having means for emitting a signal in response to changes of electric potential occurring during a heartbeat of the patient.

7. Apparatus as claimed in claim 6 further comprising:

an internal sensor transmitter electrically said at least one electrode and having means for receiving the signal from said at least one electrode; and an internal transcutaneous signal transmitter electrically coupled to said internal sensor transmitter;

the sensor transmitter having means for communicating the signal to the internal transcutaneous signal transmitter.

8. Apparatus as claimed in claim 7 further comprising:

an external transcutaneous signal transmitter proximate the patient's external chest wall and being in electrical communication with the internal transcutaneous signal transmitter; and an electrical pulse generator electrically coupled to both said external transcutaneous signal transmitter and the main pump.

9. Apparatus as claimed in claim 8 in which the electrical pulse generator includes a commutator, a timer and a power source.

10. Apparatus as claimed in claim 8 wherein:

the electrical pulse generator comprises means for sending a signal to said main pump.

11. Apparatus as claimed in claim 1 wherein said compressing means includes a diaphragm adapted to be positioned proximate the patient's atrium wall.

12. Apparatus as claimed in claim 1 wherein said restriction means comprises a flexible sleeve adapted to substantially surround the patient's inferior vena cava.

13. An apparatus to assist a patient's heart comprising:

a main pump adapted to be mounted to a patient's chest wall and including a pump chamber containing a first fluid, the main pump having means for generating a compression stroke and an expansion stroke;

an atrial pump adapted to be attached to an atrium of the patient's heart, said atrial pump including an atrial chamber containing a second fluid and means for exerting a pressure on the atrium; and means for coupling the atrial pump to the main pump so that the exerting means exerts said pressure on the atrium when the generating means generates the compression stroke to thereby pump blood towards the patient's pulmonary artery.

14. An apparatus to assist a patient's heart comprising:

a main pump adapted to be mounted to a patient's chest wall and including a pump chamber containing a first fluid, the main pump having means for generating a compression stroke and an expansion stroke to increase and decrease, respectively, a pressure force on said first fluid;

an atrial pump adapted to be attached to an atrium of the patient's heart, said atrial pump including an atrial chamber containing a second fluid;

means for transmitting said pressure force on said first fluid in said pump chamber to said second fluid in said atrial chamber, said transmitting means including a conduit fluidly coupled to said atrial chamber; and a bypass fluidly coupled to said conduit and adapted to surround the patient's inferior vena cava;

whereby the generating means generates said compression stroke to apply said increased pressure force on said first fluid which is transmitted by said transmitting means to said second fluid to both force said second fluid in the bypass to restrict the patient's inferior vena cava and said second fluid in said atrial chamber to compress the atrium to thereby pump blood towards the patient's pulmonary artery.

* * * * *